United States Patent
Nawata et al.

(10) Patent No.: US 9,040,918 B2
(45) Date of Patent: May 26, 2015

(54) TERAHERTZ WAVE DETECTION DEVICE AND METHOD

(71) Applicant: RIKEN, Saitama (JP)

(72) Inventors: Kouji Nawata, Saitama (JP); Hiroaki Minamide, Saitama (JP); Hiromasa Ito, Saitama (JP); Shin'ichiro Hayashi, Saitama (JP)

(73) Assignee: RIKEN, Saitama (JP)

( * ) Notice: Subject to any disclaimer, the term of this patent is extended or adjusted under 35 U.S.C. 154(b) by 0 days.

(21) Appl. No.: 14/249,046

(22) Filed: Apr. 9, 2014

(65) Prior Publication Data

US 2014/0299773 A1 Oct. 9, 2014

(30) Foreign Application Priority Data

Apr. 9, 2013 (JP) ................. 2013/081055

(51) Int. Cl.
| | |
|---|---|
| *G01J 5/02* | (2006.01) |
| *G01J 1/04* | (2006.01) |
| *G02F 1/365* | (2006.01) |
| *G01J 1/42* | (2006.01) |

(52) U.S. Cl.
CPC ............ *G01J 1/0425* (2013.01); *G02F 1/365* (2013.01); *G01J 1/42* (2013.01)

(58) Field of Classification Search
USPC .................................. 250/339.06
See application file for complete search history.

(56) References Cited

U.S. PATENT DOCUMENTS

| | | | | |
|---|---|---|---|---|
| 2005/0238070 | A1* | 10/2005 | Imeshev et al. | 372/21 |
| 2009/0040597 | A1* | 2/2009 | Rae et al. | 359/330 |
| 2010/0195675 | A1* | 8/2010 | Moloney et al. | 372/4 |
| 2011/0057109 | A1* | 3/2011 | Guo et al. | 250/340 |
| 2013/0128340 | A1* | 5/2013 | Rae et al. | 359/330 |

FOREIGN PATENT DOCUMENTS

| | | |
|---|---|---|
| JP | 2010210991 A | 9/2010 |
| JP | 2011075583 A | 4/2011 |
| JP | 2012014155 A | 1/2012 |

OTHER PUBLICATIONS

Sasaki et al., "Terahertz-wave surface-emitted difference frequency generation in slant-stripe-type . . .", Applied Physics Letters, Oct. 28, 2002, pp. 3323-3325, vol. 81, No. 18.

(Continued)

*Primary Examiner* — David J Makiya
*Assistant Examiner* — Taeho Jo
(74) *Attorney, Agent, or Firm* — Griffin & Szipl, P.C.

(57) ABSTRACT

The present invention includes a slanted periodically poled device 12 including a light input surface 12a and a light output surface 12b parallel to each other and a terahertz wave input surface 12c orthogonal to the light input surface 12a and the light output surface 12b, a pump beam source 14 which emits pump beam 1 perpendicularly to the light input surface 12a, and a photodetector 16 which detects an up-conversion signal beam A converted from a terahertz wave 3 emitted perpendicularly from the light output surface 12b. The slanted periodically poled device 12 is configured to generate the up-conversion signal beam A in the same direction as and in parallel with the pump beam 1 by quasi phase matching between the terahertz wave 3 perpendicularly incident from the terahertz wave input surface 12c and the pump beam 1.

14 Claims, 7 Drawing Sheets

(56) References Cited

OTHER PUBLICATIONS

Babin et al., "Use of stimulated scattering by polaritons in detection of submillimeter radiation", Soviet Journal of Quantum Electronics 13(7), Jul. 1983, pp. 958-960.

Ding et al., "Efficient THz generation and frequency upconversion in GaP crystals", Solid-State Electronics 50, 2006, pp. 1128-1136.

Guo et al., "Highly sensitive Coherant detection of terahertz waves at room temperature using a parametric process", Applied Physics Letters 93, 2008, pp. 021106-1-021106-3.

Minamide et al., "High-sensitivity detection of terahertz waves using nonlinear up-conversion in an organic . . . ", Applied Physics Letters 97, 2010, pp. 121106-1-121106-3.

* cited by examiner

TERAHERTZ WAVE DETECTION DEVICE AND METHOD

This application claim priority from Japanese Patent Application No. 2013/081055, filed Apr. 9, 2013, the entire disclosure of which is incorporated herein by reference.

BACKGROUND OF THE INVENTION

1. Field of the Invention

The present invention relates to a terahertz wave detection device and method for detecting a weak terahertz wave by using a nonlinear optical effect.

2. Background Art

The term "terahertz wave" means an electromagnetic wave whose frequency is in the range of 0.1 to 10 THz (1 THz=$10^{12}$ Hz), in other words, whose wavelength is the range from 0.03 to 3 mm of millimeter-wave to a wavelength of far-infrared.

The terahertz wave is expected to be applied in a wide range of fields extending from basic research such as radio astronomy, materials science, and biomolecular spectroscopy to practical applications such as security, information communication, environment, and medical care.

The terahertz wave, however, is an electromagnetic wave having a frequency band between light such as mid and near infrared radiation, visible light, and UV radiation (frequency: $1\times10^{13}$ to $10^{15}$ Hz) and a radio wave (frequency: $10^{3}$ to $10^{12}$ Hz), which leads to a problem that it is impossible to directly apply the existing techniques of optics and electronics to the terahertz wave.

A detection means for detecting a terahertz wave by using the nonlinear optical effect is disclosed in, for example, Patent Literatures 1 to 3.

Moreover, the documents related to the present invention are disclosed in, for example, Non-patent Literatures 1 to 5.

Non-patent Literature 1 is a document related to the generation of a terahertz wave using periodically poled device and differs from the present invention.

Moreover, Non-patent Literatures 2 to 5 relate to the detection of a terahertz wave using a bulk crystal and differ from the detection of a terahertz wave using the periodically poled device.

"A monochrome wavelength variable type terahertz wave generation/detection system and a method" in Patent Literature 1 are terahertz wave detection means using a bulk crystal having a nonlinear optical effect.

"A terahertz wave generation element, a terahertz wave detection element, and a terahertz time domain spectral instrument" in Patent Literature 2 are intended to detect a terahertz wave by irradiating a bulk crystal with an ultrashort pulse laser beam having a shorter pulse width than a picosecond ($10^{-12}$ second).

"A terahertz photodetector and optical equipment" in Patent Literature 3 use a crystal (photonic crystal) in which layers having different refractive indices are alternately combined.

Moreover, as terahertz wave detectors other than those using the nonlinear optical effect, there are known a heat detection type terahertz wave detector, a terahertz square detector, and a quantum detector.

The heat detection type terahertz wave detector corresponds to a bolometer, a pyroelectric effect detector, or a Golay cell, which detects a terahertz wave as heat energy. This type of detector is quite different from the present invention which uses the nonlinear optical effect. Typical thermal type detectors are as described below.

A detector such as a silicon bolometer operated under very low temperature of 4K has relatively high detection sensitivity. Such detector, however, needs to use liquid helium and therefore cannot be used in a versatile manner in practical application. On the other hand, a pyroelectric effect detector and a Golay cell operate at room temperature, but are lower in the detection sensitivity by more than two digits than a bolometer and have difficulty in enabling a high output of a terahertz wave light source, which often leads to a problem in use.

Moreover, these detectors basically have a low response speed such as microseconds to milliseconds and therefore cannot be used for advanced measurement such as time-resolved spectroscopy.

The terahertz square detector corresponds to, for example, a Schottky diode.

A Schottky diode with a semiconductor such as GaAs capable of operating at high speed is a terahertz wave detector which operates at room temperature and is capable of measuring a pulse whose duration is shorter than a nanosecond. Having a structure of detecting a terahertz wave via an antenna, however, the Schottky diode largely depends on the performance of the antenna. Particularly, the antenna is designed so as to be optimal in a specific frequency region, and therefore a terahertz wave cannot be detected with high efficiency over a wide band such as 1 to 3 THz. Moreover, the wavelength of the terahertz wave is short compared to a microwave or the like, and is several hundreds μm or less and therefore the terahertz wave is reduced in amplitude according to the wavelength, which causes an error at the time of manufacturing to significantly affect the performance.

Furthermore, the Schottky diode responding to high frequency has a whisker antenna and is used with the needle-like antenna in contact with a detector. In this mechanism, the contact cannot be maintained in some cases by a mechanical shock caused by vibration or the like, which leads to a problem for stable terahertz wave measurement.

The quantum detector corresponds to a quantum dot detector, a semiconductor photoconductive detector, or the like.

The quantum detector has high sensitivity and high response speed. The quantum detector, however, operates under very low temperature and therefore is not used in a versatile manner in practical application. The use of the quantum detector is limited to a narrow application such as application to astronomy requiring an ultimate performance.

CITATION LIST

Non-Patent Literatures

NPL 1: Y. Sasaki, A. Yuri, K. Kawase, and H. Ito, "Terahertz-wave surface-emitted difference frequency generation in slant-stripe-type periodically poled LiNbO$_3$ crystal," Appl. Phys. Lett. 81, 3323(2002).

NPL 2: A. A. Babin, V. N. Petryakov, and G. I. Freidman, "Use of stimulated scattering by polaritons in detection of submillimeter radiation," Soviet Journal of Quantum Electronics 13, 958-960 (1983).

NPL 3: Y. J. Ding, and W. Shi, "Efficient THz generation and frequency upconversion in GaP crystals," Solid-State Electronics 50, 1128-1136 (2006).

NPL 4: R. Guo, S. Ohno, H. Minamide, T. Ikari, and H. Ito, "Highly sensitive Coherent detection of terahertz waves at room temperature using a parametric process," Appl. Phys. Lett. 93, 021106 (2008).

NPL 5: Hiroaki Minamide, Jun Zhang, Ruixiang Guo, Katsuhiko Miyamoto, Seigo Ohno, and Hiromasa Ito, "High-sensitivity detection of terahertz waves using nonlinear up-conversion in an organic 4-dimethylamino-N-methyl-4-stilbazolium tosylate crystal," Appl. Phys. Lett. 97, 121106 (2010).

Patent Literatures

PTL 1: Japanese Patent Application Laid-Open No. 2011-75583
PTL 2: Japanese Patent Application Laid-Open No. 2012-14155
PTL 3: Japanese Patent Application Laid-Open No. 2010-210991

SUMMARY OF THE INVENTION

A conventional terahertz wave detection means which uses a nonlinear optical effect uses, for example, a lithium niobate ($LiNbO_3$) crystal as a nonlinear optical crystal. When a pump beam and a terahertz wave enter the nonlinear optical crystal, an up-conversion signal beam having different wavelengths according to the terahertz wave frequency is generated. Therefore, the terahertz wave detection means measures the intensity and frequency of the terahertz wave by detecting the intensity and wavelength of the generated up-conversion signal beam.

FIGS. 1A and 1B illustrate schematic diagrams of a conventional terahertz wave detection device which uses a nonlinear optical effect: FIG. 1A illustrates a conventional terahertz wave detection optical system; and FIG. 1B illustrates a phase matching condition.

As illustrated in FIG. 1A, to detect a terahertz wave 3 by using a bulk crystal 4 (in this example, $LiNbO_3$) having the nonlinear optical effect, the energy conservation law ($\omega_1 = \omega_2 + \omega_3$) and the momentum conservation law ($k_1 = k_2 + k_3$) as a phase matching condition (See FIG. 1B) necessary for wavelength conversion need to be satisfied at the same time in the inside of the bulk crystal 4.

Here, $\omega_1$, $\omega_2$, and $\omega_3$ indicate the angular frequency (i.e. energy) of a pump beam 1, the angular frequency of an up-conversion signal beam 2, and the angular frequency of terahertz wave 3, respectively, and $k_1$, $k_2$, and $k_3$ indicate the wave number (i.e. momentum) of the pump beam 1, the wave number of the up-conversion signal beam 2, and the wave number of the terahertz wave 3, respectively.

(1) As a result, as apparent from FIG. 1B, the up-conversion signal beam 2 advances at an angle θ which is different from the angle of the pump beam 1. Note that the angle θ is an angle formed between the up-conversion signal beam 2 and the pump beam 1.

The presence of the angle θ causes the pump beam 1 and the up-conversion signal beam 2 to separate spatially from each other as advancing in the inside of the bulk crystal 4, thus causing a region where two light waves (the pump beam 1 and the up-conversion signal beam 2) interact with each other (an interaction region) to be small. Therefore, the conventional terahertz wave detection device has a problem of low conversion efficiency in converting the terahertz wave into an up-conversion signal beam easy to detect.

(2) Moreover, the output position and angle θ of the up-conversion signal beam 2 vary with the frequency of the terahertz wave 3. Therefore, in order to guide the generated up-conversion signal beam 2 to a photodetector 5 even in the case of a change in the frequency of the terahertz wave 3, a correction optical system 6 is required in the rear stage of the bulk crystal 4, thereby increasing the entire system in size.

(3) Furthermore, the terahertz wave 3 is obliquely introduced from the side surface of the bulk crystal 4 via an input coupling element 7 such as a silicon prism. Therefore, the alignment in which the terahertz wave 3 is introduced into the interaction region causes difficulty since it is performed via the input coupling element 7 having a high refractive index and thereby suffers a significant terahertz wave introduction loss (Fresnel loss) in the input coupling element 7.

The present invention has been made to solve the above problem. Specifically, the object of the present invention is to provide a terahertz wave detection device and method capable of converting a weak terahertz wave into an up-conversion signal beam easy to detect with high efficiency by optical parametric amplification by reducing the terahertz wave introduction loss and increasing the interaction region between the pump beam and the up-conversion signal beam.

According to the present invention, there is provided a terahertz wave detection device including:
a slanted periodically poled device including a light input surface and a light output surface parallel to each other and a terahertz wave input surface orthogonal to the light input surface and the light output surface;
a pump beam source which emits a pump beam perpendicularly to the light input surface; and
a photodetector which detects an up-conversion signal beam converted from a terahertz wave perpendicularly emitted from the light output surface,
wherein the slanted periodically poled device is configured to generate the up-conversion signal beam in the same direction as and in parallel with the pump beam by quasi phase matching between a terahertz wave perpendicularly incident from the terahertz wave input surface and the pump beam.

The quasi phase matching provides a momentum to a phase matching condition by a poling angle and a poling period relative to the pump beam.

The slanted periodically poled device is preferably a periodically poled lithium niobate crystal.

The terahertz wave detection device further includes a light separation element which separates only the up-conversion signal beam from two light waves of the up-conversion signal beam and the pump beam between the slanted periodically poled device and the photodetector.

The light separation element is a semi-transparent mirror, a dielectric multilayer film filter, or a grating.

Preferably the terahertz wave detection device further includes a second harmonic generator which doubles the frequency of the up-conversion signal beam or the pump beam and which is positioned between the slanted periodically poled device and the light separation element.

The photodetector is a photodiode or a spectrum analyzer which measures the intensity or frequency of the terahertz wave.

The terahertz wave detection device further includes a sample irradiation optical system which makes a terahertz wave enter a sample so that the terahertz wave passes through the sample to become a sample wave, the sample irradiation optical system outputting the sample wave,
wherein the terahertz wave includes the sample wave and a reference wave which does not pass through the sample and the photodetector is used to measure the phase and amplitude of the terahertz wave.

The terahertz wave detection device further includes a time delay optical system which outputs a sample wave that is a delayed terahertz wave and that is produced by delaying the terahertz wave, wherein the terahertz wave includes the sample wave and a reference wave not delayed and the photodetector is used to measure the phase and amplitude of the terahertz wave.

The slanted periodically poled device is a waveguide structure of a bulk type in which the pump beam or the up-conversion signal beam is confined inside, a ridge type in which a substrate is added to the bulk type, or a slab type which includes low refractive index sections, one of which is integrated with a terahertz wave input surface of the bulk type or the ridge type and the other of which is integrated with the side surface opposed to the terahertz wave input surface, each having a refractive index smaller than a refractive index of a portion between the side surfaces.

The slanted periodically poled device includes a plurality of division elements arranged in parallel or in series; and the poling angles and the poling periods of the division elements respectively correspond to terahertz waves having frequencies different from one another.

The terahertz wave detection device further includes:

a pump beam fiber formed of an optical fiber which connects the light input surface of the slanted periodically poled device to the pump beam source;

an up-conversion signal beam fiber formed of an optical fiber which includes one end connected to the light output surface of the slanted periodically poled device; and a fiber frequency filter which is connected to the other end of the up-conversion signal beam fiber and outputs only the up-conversion signal beam to the photodetector.

Preferably the terahertz wave detection device further includes a terahertz wave fiber formed of an optical fiber which connects the terahertz wave input surface of the slanted periodically poled device to the terahertz wave light source.

Moreover, according to the present invention, there is provided a terahertz wave detection method including:

preparing a slanted periodically poled device, a pump beam source, and a photodetector wherein the slanted periodically poled device includes a light input surface and a light output surface parallel to each other and a terahertz wave input surface orthogonal to the light input surface and the light output surface, the pump beam source emits pump beam perpendicularly to the light input surface, and the photodetector detects an up-conversion signal beam converted from a terahertz wave perpendicularly emitted from the light output surface; and using the slanted periodically poled device to generate the up-conversion signal beam in the same direction as and in parallel with the pump beam by quasi phase matching between a terahertz wave perpendicularly incident from the terahertz wave input surface and the pump beam.

According to the device and method of the present invention, the slanted periodically poled device is configured to generate the up-conversion signal beam in the same direction as and in parallel with the pump beam by the quasi phase matching between the terahertz wave perpendicularly incident from the terahertz wave input surface and the pump beam perpendicularly incident from the light input surface. Therefore, the terahertz wave introduction loss is able to be reduced by omitting the input coupling element and the up-conversion signal beam is able to be generated and propagated in the same direction as the pump beam.

The up-conversion signal beam propagating in the same direction as the pump beam in the inside of the slanted periodically poled device (in the optical waveguide) satisfies the phase matching condition and therefore is amplified by the pump beam through optical parametric amplification. The optical parametric amplification continues from the incident position of the terahertz wave to the light output surface of the slanted periodically poled device, thereby enabling an increase in the interaction region between the pump beam and the up-conversion signal beam and remarkable enhancement of the conversion efficiency in converting the terahertz wave into the up-conversion signal beam.

Therefore, according to the present invention, a weak terahertz wave is able to be converted into an up-conversion signal beam easy to detect with high efficiency through the optical parametric amplification by reducing the terahertz wave introduction loss and increasing the interaction region between the pump beam and the up-conversion signal beam.

DESCRIPTION OF THE PREFERRED EMBODIMENTS

Figure 1A:
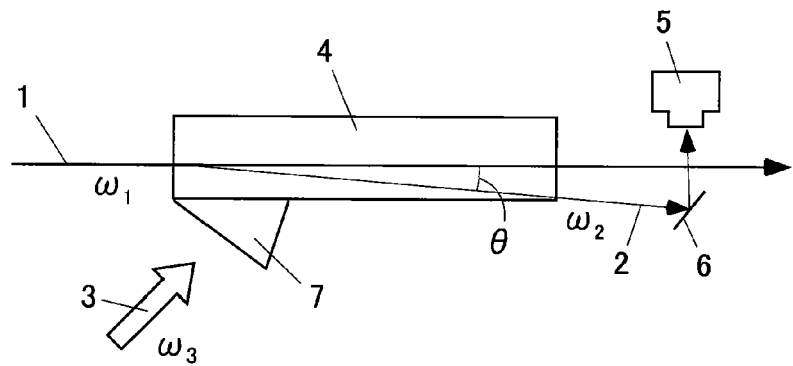
FIG. 1A is a schematic diagram of a conventional terahertz wave detection device which uses a nonlinear optical effect.
Figure 1B:
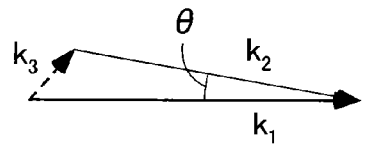
FIG. 1B is a diagram illustrating a conventional phase matching condition.

The preferred embodiments of the present invention will now be described in detail hereinafter with reference to the accompanying drawings. The same reference numerals refer to the same parts throughout the various figures and redundant description will be omitted.

Figure 2A:
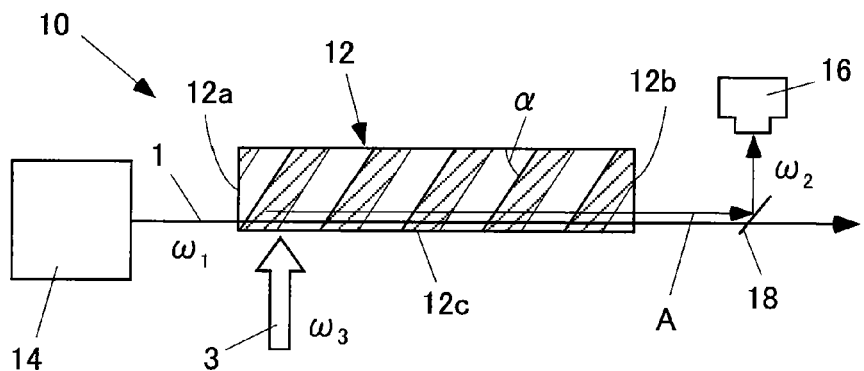
FIG. 2A is a diagram illustrating a first embodiment of a terahertz wave detection device according to the present invention.
Figure 2B:
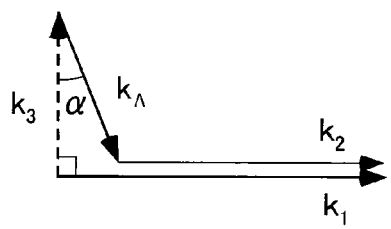
FIG. 2B is a diagram illustrating a phase matching condition of the present invention.

FIGS. 2A and 2B are diagrams illustrating a first embodiment of a terahertz wave detection device 10 according to the present invention. FIG. 2A illustrates a terahertz wave detection optical system of the present invention. FIG. 2B illustrates a phase matching condition of the present invention.

In FIG. 2A, the terahertz wave detection device 10 of the present invention includes a slanted periodically poled device 12, a pump beam source 14, and a photodetector 16.

The slanted periodically poled device 12 has a light input surface 12a and a light output surface 12b, which are parallel to each other, and a terahertz wave input surface 12c orthogonal to the light input surface 12a and the light output surface 12b.

The pump beam source 14 emits a pump beam 1 to the light input surface 12a in a direction perpendicular to the light input surface 12a of the slanted periodically poled device 12.

The photodetector 16 detects an up-conversion signal beam A converted from a terahertz wave 3 that is emitted from the light output surface 12b in a direction perpendicular to the light output surface 12b of the slanted periodically poled device 12.

The pump beam 1 is preferably an infrared laser beam having a wavelength of 1 to 10 μm or a visible laser beam. Hereinafter, the infrared laser beam having a wavelength of 1 to 10 μm or the visible laser beam is referred to as "light wave."

The slanted periodically poled device 12 is a periodically poled lithium niobate crystal in this example.

The terahertz wave input surface 12c of the slanted periodically poled device 12 is configured to generate the up-conversion signal beam A in the same direction as and in parallel with the pump beam 1 by quasi phase matching between the terahertz wave 3 perpendicularly incident from the terahertz wave input surface 12c and the pump beam 1.

The quasi phase matching provides a momentum $k_\Lambda$ to the phase matching condition by the poling angle $\mu(°)$ and the poling period $\Lambda$ (μm) relative to the pump beam 1.

The quasi phase matching can be expressed by the following equations:

$$k_\Lambda \sin\alpha = k_1 - k_2 \quad (1)$$

$$k_\Lambda \cos\alpha = k_3 \quad (2)$$

$$k_\Lambda = 2\pi/\Lambda \quad (3)$$

$$k_j = \omega_j n_j/c \quad (4)$$

where $k_\Lambda$ is a grating wave number, j is an integer of 1, 2, or 3, ω is an angular frequency, n is a refractive index of the element for the angular frequency, and c is a light speed.

Moreover, in a terahertz wave detection method according to the present invention, as illustrated in FIG. 2A, there are prepared the slanted periodically poled device 12 having the light input surface 12a and the light output surface 12b, which are parallel to each other, and the terahertz wave input surface 12c orthogonal to the light input surface 12a and the light output surface 12b, the pump beam source 14 which emits the pump beam 1 perpendicularly to the light input surface 12a, and the photodetector 16 which detects the up-conversion signal beam A converted from the terahertz wave 3 emitted perpendicularly from the light output surface 12b.

Moreover, the slanted periodically poled device 12 is configured to generate the up-conversion signal beam A in the same direction as and in parallel with the pump beam 1 by the quasi phase matching between the terahertz wave 3 perpendicularly incident from the terahertz wave input surface 12c and the pump beam 1.

If the pump beam 1 is a light wave (an infrared laser beam having a wavelength of 1 to 10 μm or a visible laser beam), the up-conversion signal beam A is a light wave, too.

In FIG. 2A, the terahertz wave detection device 10 according to the present invention further includes a light separation element 18 which separates only the up-conversion signal beam A from two light waves of the up-conversion signal beam A and the pump beam 1 in a location between the slanted periodically poled device 12 and the photodetector 16.

The light separation element 18 is a semi-transparent mirror which transmits the pump beam 1 and reflects the up-conversion signal beam A in this example.

In FIG. 2A, the poled portions of the slanted periodically poled device 12 are indicated by shaded areas.

The slanted periodically poled device 12 is able to provide a momentum $k_\Lambda$ to the phase matching condition by the poling angle α (°) and the poling period Λ (μm) (see the phase matching condition in FIG. 2B). This quasi phase matching enables the up-conversion signal beam A to be generated collinearly (in parallel) with the pump beam 1, thereby achieving a large interaction region. As a result, optical parametric amplification continues from the incident position of the terahertz wave 3 to the light output surface 12b of the slanted periodically poled device 12, thereby achieving a high conversion efficiency of a conversion from the terahertz wave 3 to the up-conversion signal beam A.

In this regard, the term "optical parametric amplification" means a phenomenon that the up-conversion signal beam A is amplified by the energy of the pump beam 1 since the up-conversion signal beam A propagates in the same direction as the pump beam 1 in the inside of the slanted periodically poled device 12 (in the optical waveguide).

Moreover, the terahertz wave 3 can be made incident perpendicularly from the terahertz wave input surface 12c of the slanted periodically poled device 12 and therefore the input coupling element 7 (see FIG. 1A) is no longer required, thereby eliminating the terahertz wave introduction loss (Fresnel loss) caused by the input coupling element 7.

Figure 3:
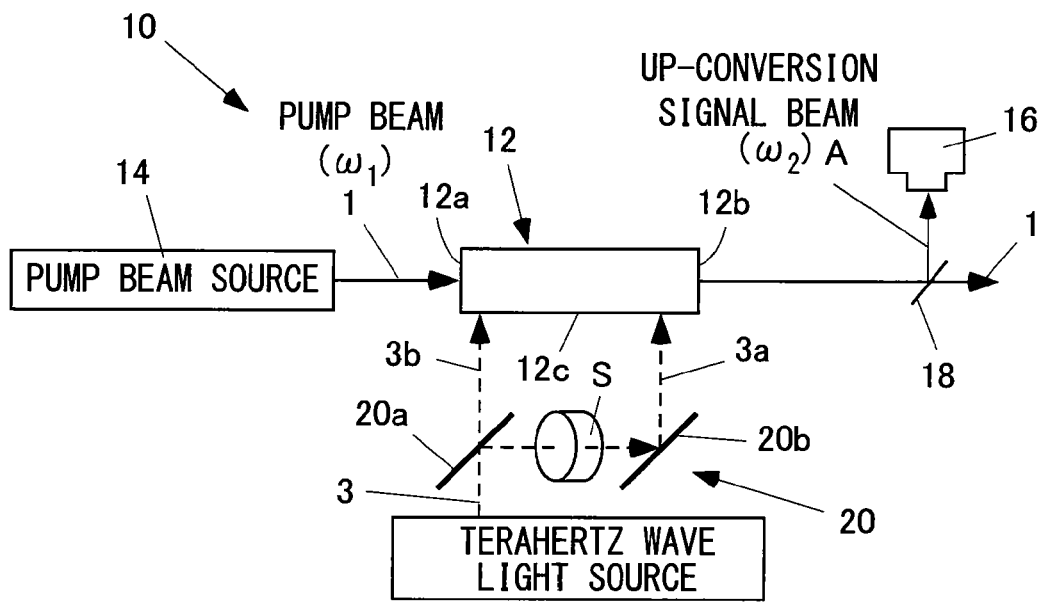
FIG. 3 is a diagram illustrating a second embodiment of the terahertz wave detection device according to the present invention.

FIG. 3 is a diagram illustrating a second embodiment of the terahertz wave detection device 10 according to the present invention.

In this diagram, the terahertz wave detection device 10 according to the present invention further includes a sample irradiation optical system 20 causes a terahertz wave 3 to enter a sample S so that the terahertz wave 3 passes through the sample S to become a sample wave 3a. The sample irradiation optical system 20 outputs the sample wave 3a.

The sample irradiation optical system 20, in this example, includes a first mirror 20a which reflects a part of the terahertz wave 3 that will perpendicularly enter the terahertz wave input surface 12c of the slanted periodically poled device 12 such that the reflected part of the terahertz wave 3 propagates to the sample S. The sample irradiation optical system 20 also includes a second mirror 20b which reflects the terahertz wave 3 having passed through the sample S (referred to as "sample wave 3a") toward the terahertz wave input surface 12c of the slanted periodically poled device 12.

According to this configuration, the terahertz wave 3 perpendicularly incident on the terahertz wave input surface 12c of the slanted periodically poled device 12 is composed of the sample wave 3a and a reference wave 3b which does not pass through the sample S.

Moreover, the photodetector 16 is a photodiode or a spectrum analyzer which measures the intensity or frequency of the terahertz wave 3 (the sample wave 3a and the reference wave 3b).

The configuration of the terahertz wave detection device 10 in FIG. 3 enables the terahertz wave 3 to be dispersed for measurement of the phase and amplitude of the terahertz wave 3.

Moreover, this configuration enables the terahertz wave detection device 10 to be used as an optical modulator using a terahertz wave.

Figure 4:
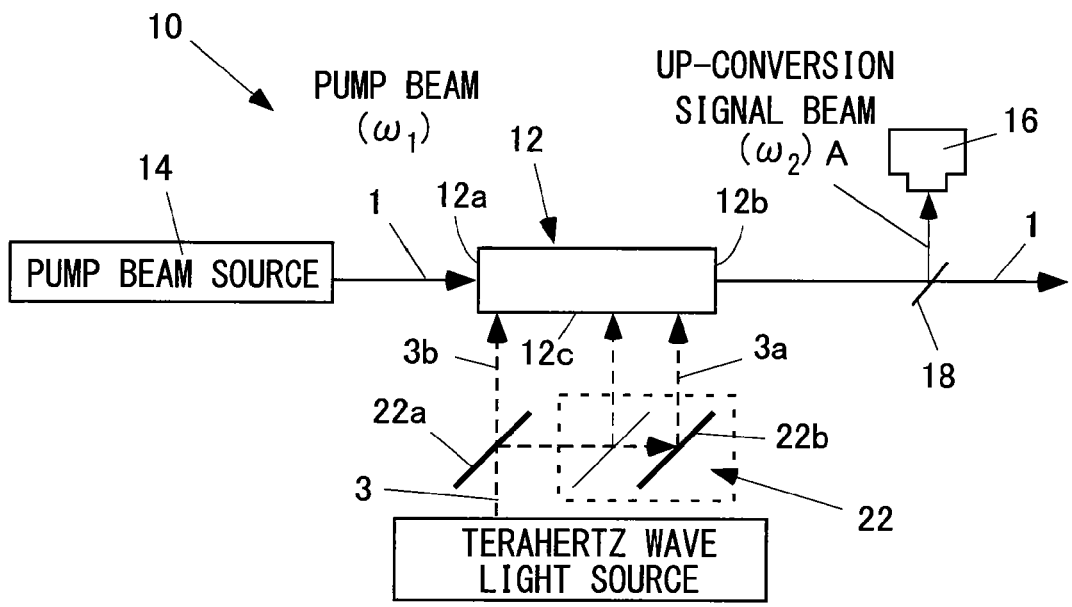
FIG. 4 is a diagram illustrating a third embodiment of the terahertz wave detection device according to the present invention.

FIG. 4 is a diagram illustrating a third embodiment of the terahertz wave detection device 10 according to the present invention.

In this diagram, the terahertz wave detection device 10 according to the present invention further includes a time delay optical system 22 which outputs a sample wave 3a that is a delayed terahertz wave 3 and that is produced by delaying the terahertz wave 3.

The time delay optical system 22 includes a first mirror 22a which reflects a part of the terahertz wave 3 that will perpendicularly enter the terahertz wave input surface 12c of the slanted periodically poled device 12. The reflected part of the terahertz wave 3 propagates in a direction other than a direction toward the terahertz wave input surface 12c. The time delay optical system 22 also includes a second mirror 22b which reflects the terahertz wave 3 (referred to as "sample wave 3a") reflected by the first mirror 22a toward the terahertz wave input surface 12c of the slanted periodically poled device 12.

The second mirror 22b is movable relative to the first mirror 22a and the movement of the second mirror 22b delays the sample wave 3a relative to the terahertz wave 3 (referred to as "reference wave 3b") directly incident on the terahertz wave input surface 12c.

The configuration of the terahertz wave detection device 10 in FIG. 4 enables the phase and amplitude of the terahertz wave 3 to be measured by using the time delay optical system 22.

Moreover, this configuration also enables the terahertz wave detection device 10 to be used as an optical modulator using a terahertz wave.

Figure 5A:
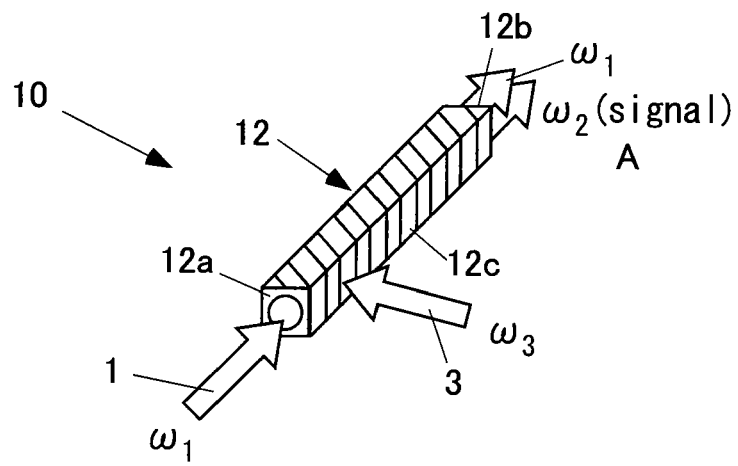
FIG. 5A is a diagram illustrating a bulk type waveguide structure in a fourth embodiment of the terahertz wave detection device according to the present invention.
Figure 5B:
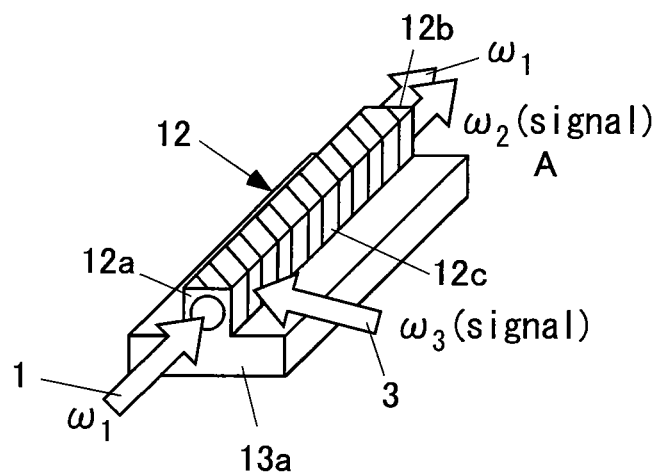
FIG. 5B is a diagram illustrating a ridge type waveguide structure in the fourth embodiment of the terahertz wave detection device according to the present invention.
Figure 5C:
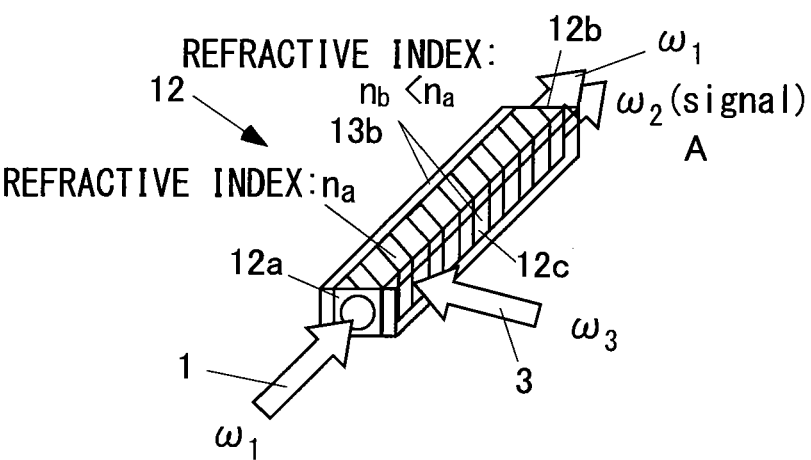
FIG. 5C is a diagram illustrating a slab type waveguide structure in the fourth embodiment of the terahertz wave detection device according to the present invention.

FIGS. 5A, 5B, and 5C are diagrams each illustrating a fourth embodiment of the terahertz wave detection device 10 according to the present invention.

In the diagrams, the slanted periodically poled device 12 is a bulk type (FIG. 5A), ridge type (FIG. 5B), or slab type (FIG. 5C) waveguide structure.

The bulk type (FIG. 5A) waveguide structure is configured to totally reflect and confine the pump beam 1 or the up-conversion signal beam A in the inside of the waveguide structure.

The ridge type (FIG. 5B) waveguide structure is formed by adding a substrate 13a to the bulk type (FIG. 5A) and is configured to totally reflect and confine the pump beam 1 or the up-conversion signal beam A in the inside of the waveguide structure like the bulk type (FIG. 5A).

The slab type (FIG. 5C) waveguide structure includes low refractive index sections 13b, one of which is integrated with the terahertz wave input surface 12c of the bulk type (FIG. 5A) or the ridge type (FIG. 5B) and the other of which is integrated with the side surface opposed to the terahertz wave input surface 12c, each having a refractive index $n_b$ smaller than a refractive index $n_a$ of a portion between the side surfaces.

In the case of the waveguide structure of the ridge type (FIG. 5B) or the slab type (FIG. 5C), the light waves (the pump beam 1 and the up-conversion signal beam A) are confined in the inside of the slanted periodically poled device 12. According to this configuration, the light waves confined in a narrow region satisfy the phase matching condition and therefore induce a nonlinear optical effect in which the optical parametric amplification is performed by the pump beam 1, thereby enabling the up-conversion signal beam A to be generated with high efficiency.

Figure 6A:
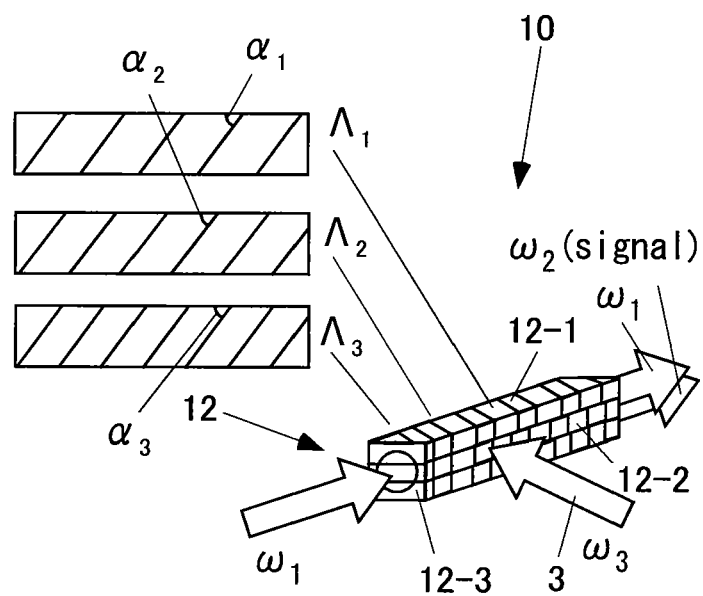
FIG. 6A is a configuration diagram of a slanted periodically poled device in a fifth embodiment of the terahertz wave detection device according to the present invention.

FIG. 6A is a diagram illustrating a fifth embodiment of the terahertz wave detection device 10 according to the present invention. FIG. 6A is a configuration diagram of a slanted periodically poled device 12 and FIG. 6B is a relation diagram between the frequency f of the terahertz wave 3 and the poling angle α and period Λ.

In FIG. 6A, the slanted periodically poled device 12 includes a plurality of division elements 12-1, 12-2, and 12-3 arranged in parallel.

The poling angles α and the poling periods Λ of the division elements 12-1, 12-2, and 12-3 respectively correspond to terahertz waves 3 having frequencies different from one another.

Figure 6B:
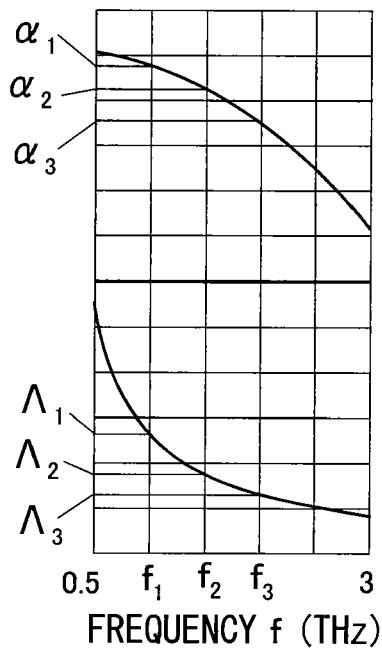
FIG. 6B is a relation diagram between the frequency of a terahertz wave and the poling angle and period.

FIG. 6B illustrates a result of calculating the poling angle α (°) and the poling period Λ (μm) where phase matching is achieved for a terahertz wave 3 having a frequency of 0.5 THz to 3 THz. When the input terahertz-wave frequencies are $f_1$, $f_2$, and $f_3$, the poling angles ($α_1$, $α_2$, $α_3$) and the poling periods ($Λ_1$, $Λ_2$, $Λ_3$) are known from FIG. 6B. Therefore, as illustrated in FIG. 6A, the frequencies $f_1$, $f_2$, and $f_3$ of the terahertz waves 3 are able to be detected by fabricating a slanted periodically poled device 12 in which three division elements 12-1, 12-2, and 12-3 corresponding to the frequencies ($f_1$, $f_2$, and $f_3$), respectively, are superimposed.

Moreover, the division elements are not limited to three elements. Terahertz waves 3 in a wide band can be detected by further increasing the division elements which are superimposed.

Figure 7A:
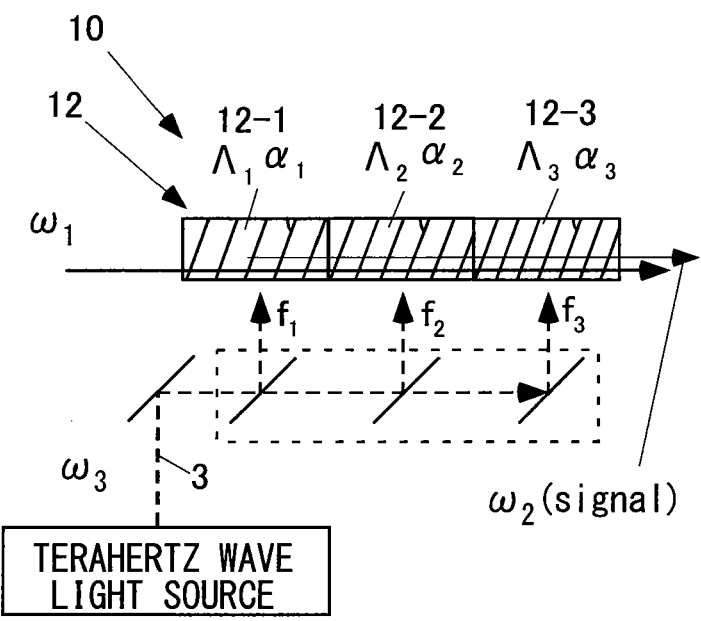
FIG. 7A is a configuration diagram of the slanted periodically poled device in a sixth embodiment of the terahertz wave detection device according to the present invention.
Figure 7B:
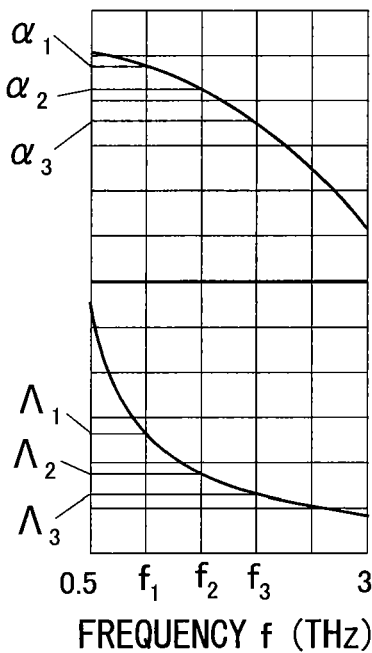
FIG. 7B is a relation diagram between the frequency of a terahertz wave and the poling angle and period.

FIG. 7A is a diagram illustrating a sixth embodiment of the terahertz wave detection device 10 according to the present invention. FIG. 7A is the configuration diagram of the slanted periodically poled device 12 and FIG. 7B is a relation diagram between the frequency f of the terahertz wave 3 and the poling angle α and period Λ.

In FIG. 7A, the slanted periodically poled device 12 includes a plurality of division elements 12-1, 12-2, and 12-3 arranged in series.

The poling angles α (°) and periods Λ (μm) of the division elements 12-1, 12-2, and 12-3 respectively correspond to terahertz waves 3 having frequencies different from one another.

Other aspects of the configuration are the same as those illustrated in FIG. 6A.

According to the configuration, terahertz waves 3 in a wide band can be detected like FIG. 6A also in the case where the division elements 12-1, 12-2, and 12-3 are arranged in series.

Figure 8A:
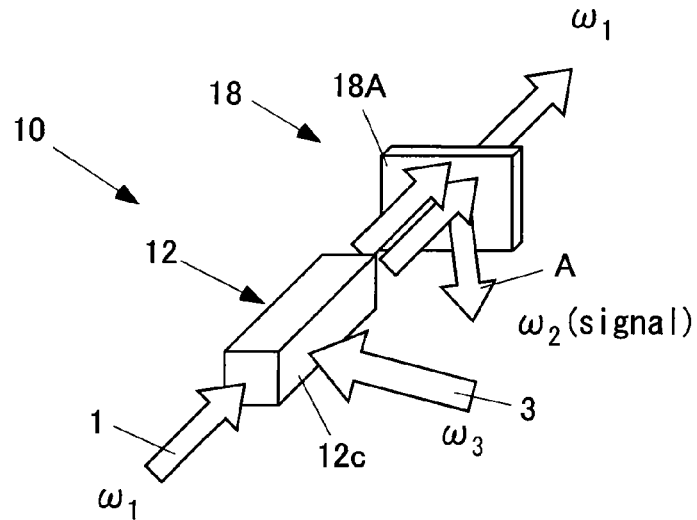
FIG. 8A is a diagram illustrating a seventh embodiment of the terahertz wave detection device according to the present invention.
Figure 8B:
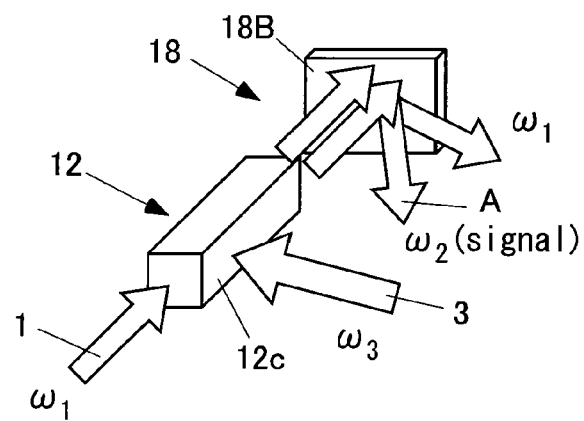
FIG. 8B is another diagram illustrating the seventh embodiment of the terahertz wave detection device according to the present invention.
Figure 8C:
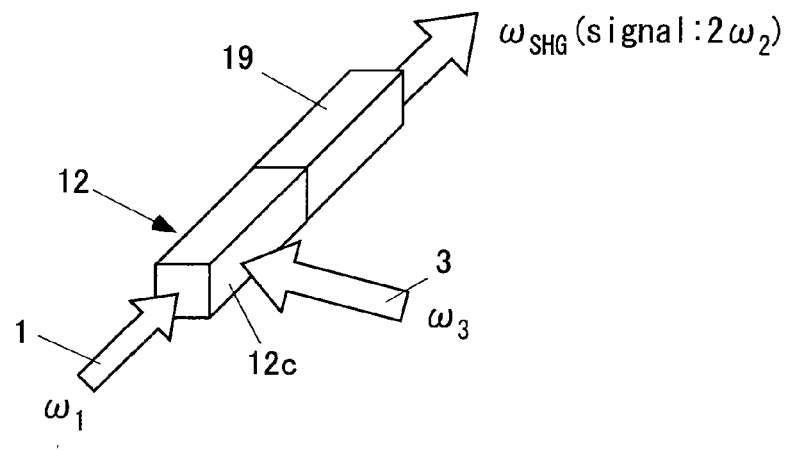
FIG. 8C is a still another diagram illustrating the seventh embodiment of the terahertz wave detection device according to the present invention.

FIGS. 8A, 8B, and 8C are diagrams illustrating a seventh embodiment of the terahertz wave detection device 10 according to the present invention.

The light separation element 18 is a dielectric multilayer film filter 18A in FIG. 8A and a grating 18B in FIG. 8B.

In the present invention, the pump beam 1 and the up-conversion signal beam A propagate collinearly, and therefore it is preferable to separate the two light waves of the pump beam 1 and the up-conversion signal beam A in terms of space or frequency and to thereafter introduce the separated light waves into the photodetector 16.

As illustrated in FIGS. 8A and 8B, it is preferable to provide a dielectric multilayer film filter 18A or a grating 18B in the rear stage of the slanted periodically poled device 12 as the light separation element 18 for separating the two light waves of the pump beam 1 and the up-conversion signal beam A. The separated up-conversion signal beam A is detected by the photodetector 16.

Moreover, in FIG. 8C, the reference numeral 19 indicates a second harmonic generator.

The second harmonic generator 19 is provided between the slanted periodically poled device 12 and the light separation element 18 (not illustrated) and preferably doubles the frequency of the up-conversion signal beam A or the pump beam 1.

This configuration enables the frequency of the up-conversion signal beam A or the pump beam 1 to be doubled to convert the wavelength into a wavelength (for example, a wavelength of visible light) easy to detect by the photodetector 16.

Figure 9:
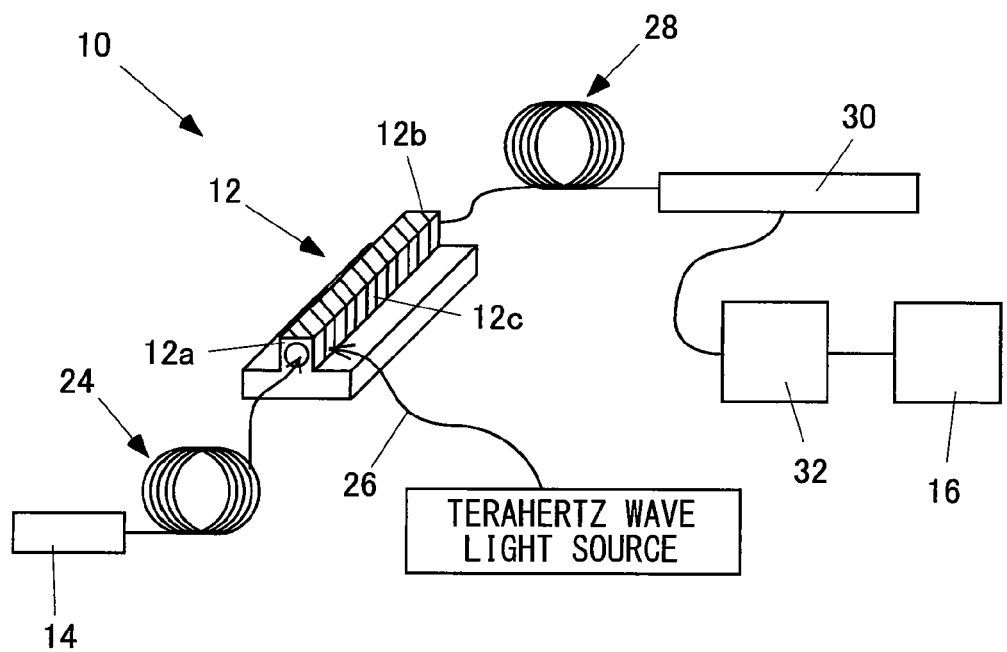
FIG. 9 is a diagram illustrating an eighth embodiment of the terahertz wave detection device according to the present invention.

FIG. 9 is a diagram illustrating an eighth embodiment of the terahertz wave detection device 10 according to the present invention.

In this diagram, the terahertz wave detection device 10 according to the present invention further includes pump beam fiber 24, a terahertz wave fiber 26, an up-conversion signal beam fiber 28, and a fiber frequency filter 30.

The pump beam fiber 24 is formed of an optical fiber which connects the light input surface 12a of the slanted periodically poled device 12 to the pump beam source 14.

The terahertz wave fiber 26 is formed of an optical fiber which connects the terahertz wave input surface 12c of the slanted periodically poled device 12 to the terahertz wave light source.

Note that the terahertz wave fiber 26 is optional and may be omitted.

The up-conversion signal beam fiber 28 is formed of an optical fiber having one end connected to the light output surface 12b of the slanted periodically poled device 12.

The fiber frequency filter 30 is connected to the other end of the up-conversion signal beam fiber 28 and outputs only the up-conversion signal beam A to the photodetector 16.

In FIG. 9, the pump beam 1 and the terahertz wave 3 are introduced into the slanted periodically poled device 12 via the pump beam fiber 24 and the terahertz wave fiber 26, respectively. The two light waves (the pump beam 1 and the up-conversion signal beam A) output from the slanted periodically poled device 12 are connected to the up-conversion signal beam fiber 28 and introduced into the fiber frequency filter 30. The fiber frequency filter 30 extracts only the up-conversion signal beam A and the photodetector 16 detects the up-conversion signal beam A. In this process, a fiber amplifier 32 amplifies the up-conversion signal beam A and thereafter the photodetector 16 measures the amplified up-conversion signal beam A, thereby enabling weak up-conversion signal beam A to be detected. As a result, the detection sensitivity of the terahertz wave 3 can be improved.

Moreover, in the configuration illustrated in FIG. 9, the pump beam fiber 24 and the up-conversion signal beam fiber 28 have low loss of the light waves, thereby enabling the transmission distance to be long (for example, several tens of meters to several kilometers). Therefore, the phase and amplitude of the terahertz wave 3 are able to be measured from a remote place by amplifying or modulating the terahertz wave 3 using the slanted periodically poled device 12.

This configuration enables the terahertz wave detection device 10 according to the present invention to be applied to an optical fiber network. Moreover, in this application, it is possible to use the two light waves (the pump beam 1 and the up-conversion signal beam A) as transmission waves and the terahertz wave 3 as a modulation wave.

According to the aforementioned device and method of the present invention, the slanted periodically poled device 12 is configured to generate the up-conversion signal beam A in the same direction as and in parallel with the pump beam 1 by the quasi phase matching between the terahertz wave 3 perpendicularly incident from the terahertz wave input surface 12c and the pump beam 1 perpendicularly incident from the light input surface 12a. Therefore, a terahertz wave introduction loss can be reduced by omitting the input coupling element 7 and the up-conversion signal beam A can be generated and propagated in the same direction as the pump beam 1.

The up-conversion signal beam A propagating in the same direction as the pump beam 1 in the inside of the slanted periodically poled device 12 (in the optical waveguide) satisfies the phase matching condition and therefore is amplified by the pump beam 1 through the optical parametric amplification. The optical parametric amplification continues from the incident position of the terahertz wave 3 to the light output surface 12b of the slanted periodically poled device 12 and therefore is able to enlarge the interaction region between the pump beam 1 and the up-conversion signal beam A, thereby enabling a remarkable increase in the conversion efficiency in converting the terahertz wave 3 to the up-conversion signal beam A.

Therefore, according to the present invention, it is possible to reduce the terahertz wave introduction loss and to convert a weak terahertz wave 3 into an up-conversion signal beam A easy to detect with high efficiency through the optical parametric amplification by enlarging the interaction region between the pump beam 1 and the up-conversion signal beam A.

Moreover, according to the above embodiment of the present invention, the associated advantageous effects described below can also be achieved.

According to the configuration illustrated in FIG. 3, the intensity or frequency of the terahertz wave 3 is able to be measured by dispersing the terahertz wave 3.

According to the configuration illustrated in FIG. 4, the phase of the terahertz wave 3 is able to be measured.

According to the configurations illustrated in FIGS. 6A and 7A, terahertz waves 3 having frequencies different from one another are able to be detected.

According to the configuration illustrated in FIG. 9, fusion with an optical fiber technology enables downsizing and stabilization. In addition, higher efficiency is achieved by using an optical waveguide technology.

The present invention is not limited to the above examples and embodiments, and naturally it is intended to include various variations and modifications within the spirit and scope of the invention.

REFERENCE SIGNS LIST

α ($α_1$, $α_2$, $α_3$) Poling angle
Λ ($Λ_1$, $Λ_2$, $Λ_3$) Poling period
$k_A$ Momentum
A Up-conversion signal beam
S Sample
f ($f_1$, $f_2$, $f_3$) Frequency
1 Pump beam
2 Up-conversion signal beam
3 Terahertz wave
3a Sample wave
3b Reference wave 4 Bulk crystal
5 Photodetector
6 Correction optical system
7 Input coupling element
10 Terahertz wave detection device
12 Slanted periodically poled device (periodically poled lithium niobate crystal)
12-1, 12-2, 12-3 Division element
12a Light input surface
12b Light output surface
12c Terahertz wave input surface
13a Substrate
13b Low refractive index section
14 Pump beam source
16 Photodetector (photodiode, spectrum analyzer)
18 Light separation element
18A Dielectric multilayer film filter
18B Grating
19 Second harmonic generator
20 Sample irradiation optical system
20a First mirror
20b Second mirror
22 Time delay optical system
22a First mirror
22b Second mirror
24 Pump beam fiber
26 Terahertz wave fiber
28 Up-conversion signal beam fiber
30 Fiber frequency filter

What is claimed is:

1. A terahertz wave detection device comprising:
a slanted periodically poled device including a light input surface and a light output surface parallel to each other and a terahertz wave input surface orthogonal to the light input surface and the light output surface;
a pump beam source which emits a pump beam perpendicularly to the light input surface; and
a photodetector which detects an up-conversion signal beam converted from a terahertz wave perpendicularly emitted from the light output surface,
wherein the slanted periodically poled device is configured to generate the up-conversion signal beam in the same direction as and in parallel with the pump beam by quasi phase matching between a terahertz wave perpendicularly incident from the terahertz wave input surface and the pump beam.

2. The terahertz wave detection device according to claim 1, wherein the quasi phase matching provides a momentum to a phase matching condition by a poling angle and a poling period relative to the pump beam.

3. The terahertz wave detection device according to claim 2, wherein:
the slanted periodically poled device includes a plurality of division elements arranged in parallel or in series; and
the poling angles and the poling periods of the division elements respectively correspond to terahertz waves having frequencies different from one another.

4. The terahertz wave detection device according to claim 1, wherein the slanted periodically poled device is a periodically poled lithium niobate crystal.

5. The terahertz wave detection device according to claim 1, further comprising a light separation element which separates only the up-conversion signal beam from two light waves of the up-conversion signal beam and the pump beam between the slanted periodically poled device and the photodetector.

6. The terahertz wave detection device according to claim 5, wherein the light separation element is a semi-transparent mirror, a dielectric multilayer film filter, or a grating.

7. The terahertz wave detection device according to claim 6, further comprising a second harmonic generator which doubles the frequency of the up-conversion signal beam or the pump beam between the slanted periodically poled device and the light separation element.

8. The terahertz wave detection device according to claim 1, wherein the photodetector is a photodiode or a spectrum analyzer which measures the intensity or frequency of the terahertz wave.

9. The terahertz wave detection device according to claim 1, further comprising a sample irradiation optical system which makes a terahertz wave enter a sample so that the terahertz wave passes through the sample to become a sample wave, the sample irradiation optical system outputting the sample wave,
wherein the terahertz wave includes the sample wave and a reference wave which does not pass through the sample and the photodetector is used to measure the phase and amplitude of the terahertz wave.

10. The terahertz wave detection device according to claim 1, further comprising a time delay optical system which outputs a sample wave that is a delayed terahertz wave and that is produced by delaying the terahertz wave,
wherein the terahertz wave includes the sample wave and a reference wave not delayed and the photodetector is used to measure the phase and amplitude of the terahertz wave.

11. The terahertz wave detection device according to claim 1, wherein the slanted periodically poled device is a waveguide structure of a bulk type in which the pump beam or the up-conversion signal beam is confined inside, a ridge type in which a substrate is added to the bulk type, or a slab type which includes low refractive index sections, one of which is integrated with a terahertz wave input surface of the bulk type or the ridge type and the other of which is integrated with the side surface opposed to the terahertz wave input surface, each having a refractive index smaller than a refractive index of a portion between the side surfaces.

12. The terahertz wave detection device according to claim 1, further comprising:
a pump beam fiber formed of an optical fiber which connects the light input surface of the slanted periodically poled device to the pump beam source;
an up-conversion signal beam fiber formed of an optical fiber which includes one end connected to the light output surface of the slanted periodically poled device; and
a fiber frequency filter which is connected to the other end of the up-conversion signal beam fiber and outputs only the up-conversion signal beam to the photodetector.

13. The terahertz wave detection device according to claim 12, further comprising a terahertz wave fiber formed of an optical fiber which connects the terahertz wave input surface of the slanted periodically poled device to the terahertz wave light source.

14. A terahertz wave detection method comprising:
preparing a slanted periodically poled device, a pump beam source, and a photodetector wherein the slanted periodically poled device includes a light input surface and a light output surface parallel to each other and a terahertz wave input surface orthogonal to the light input surface and the light output surface, the pump beam source emits pump beam perpendicularly to the light input surface, and the photodetector detects an up-conversion signal beam converted from a terahertz wave perpendicularly emitted from the light output surface; and using the slanted periodically poled device to generate the up-conversion signal beam in the same direction as and in parallel with the pump beam by quasi phase matching between a terahertz wave perpendicularly incident from the terahertz wave input surface and the pump beam.

* * * * *